(12) United States Patent
Moon et al.

(10) Patent No.: US 10,758,142 B2
(45) Date of Patent: Sep. 1, 2020

(54) APPARATUS AND METHOD OF REAL-TIME HEALTH AND EXERCISE SENSOR MECHANISM WITH BIOPOTENTIAL ELECTRODE INTEGRATED DOUBLE 3D GYROSCOPE NETWORK

(71) Applicant: San Diego State University Research Foundation, San Diego, CA (US)

(72) Inventors: Kee S. Moon, San Diego, CA (US); Sung Q. Lee, Seoul (KR); Woosub Youm, Seoul (KR)

(73) Assignees: San Diego State University Research Foundation, San Diego, CA (US); Electronic and Telecommunication Research Institute, Daejeon (KR)

(*) Notice: Subject to any disclaimer, the term of this patent is extended or adjusted under 35 U.S.C. 154(b) by 244 days.

(21) Appl. No.: 16/035,605

(22) Filed: Jul. 14, 2018

(65) Prior Publication Data
US 2019/0015005 A1 Jan. 17, 2019

Related U.S. Application Data

(60) Provisional application No. 62/533,633, filed on Jul. 17, 2017.

(51) Int. Cl.
*A61B 5/0408* (2006.01)
*A61B 5/00* (2006.01)
(Continued)

(52) U.S. Cl.
CPC .............. *A61B 5/0408* (2013.01); *A61B 5/01* (2013.01); *A61B 5/04085* (2013.01); *A61B 5/113* (2013.01); *A61B 5/1121* (2013.01); *A61B 5/4818* (2013.01); *A61B 5/686* (2013.01); *A61B 5/6823* (2013.01); *A61B 5/721* (2013.01); *A61B 5/7207* (2013.01); *A61N 1/36114* (2013.01); *A61N 1/36139* (2013.01); *A61N 1/36146* (2013.01); *A61N 1/375* (2013.01); *A61N 1/37211* (2013.01); *G16H 20/30* (2018.01); *G16H 40/63* (2018.01); *H01M 2/1022* (2013.01); *H01M 10/425* (2013.01); *H02J 50/20* (2016.02); *A61B 5/0006* (2013.01);
(Continued)

(58) Field of Classification Search
CPC ..... A61B 5/0408; A61B 5/4818; A61B 5/721; A61N 1/375; A61N 1/36146
USPC ........................................................ 600/301
See application file for complete search history.

(56) References Cited

U.S. PATENT DOCUMENTS

| | | | |
|---|---|---|---|
| 2016/0113526 A1* | 4/2016 | Nageshwar | A61B 5/02433 600/473 |
| 2017/0055851 A1* | 3/2017 | Al-Ali | A61B 5/0004 |

* cited by examiner

*Primary Examiner* — Amanda K Hulbert
*Assistant Examiner* — Philip C Edwards
(74) *Attorney, Agent, or Firm* — Juneau & Mitchell; Todd L. Juneau

(57) ABSTRACT

A device and method is described for electronic human prosthetics, and specifically a body-machine interface (BMI) device where the input, output and on-board computing are combined into a single unit to form a compact ECG, respiratory sensing, temperature-sensing-prosthetics device. The devices (BMIs) can also communicate with other body-machine interface devices (BMI) and/or with external controllers wirelessly. The compact device has ultrasonic battery charging system. One or more BMI can be wirelessly connected so that a closed loop of BMIs, or a BMI and an external controller, can wirelessly send trigger pulses to the stimulator over the heart, glossopharyngeal nerve(s) or diaphragm.

34 Claims, 13 Drawing Sheets

(51) Int. Cl.
*H02J 50/20* (2016.01)
*A61B 5/01* (2006.01)
*G16H 40/63* (2018.01)
*H01M 10/42* (2006.01)
*H01M 2/10* (2006.01)
*A61N 1/375* (2006.01)
*A61N 1/36* (2006.01)
*G16H 20/30* (2018.01)
*A61N 1/372* (2006.01)
*A61B 5/11* (2006.01)
*A61B 5/113* (2006.01)
*A61N 1/362* (2006.01)
*H04W 4/80* (2018.01)
*H01M 10/0525* (2010.01)
*H02J 7/02* (2016.01)
*A61F 2/72* (2006.01)
*H02J 50/15* (2016.01)

(52) U.S. Cl.
CPC .......... *A61B 5/0008* (2013.01); *A61B 5/0022* (2013.01); *A61B 5/0031* (2013.01); *A61B 2560/0219* (2013.01); *A61B 2562/0219* (2013.01); *A61B 2562/04* (2013.01); *A61B 2562/16* (2013.01); *A61F 2/72* (2013.01); *A61N 1/362* (2013.01); *A61N 1/37217* (2013.01); *A61N 1/37235* (2013.01); *H01M 10/0525* (2013.01); *H01M 2010/4278* (2013.01); *H01M 2220/30* (2013.01); *H02J 7/025* (2013.01); *H02J 50/15* (2016.02); *H04W 4/80* (2018.02)

FIGURE 12 - Xilinx Zynq-7000 SoC
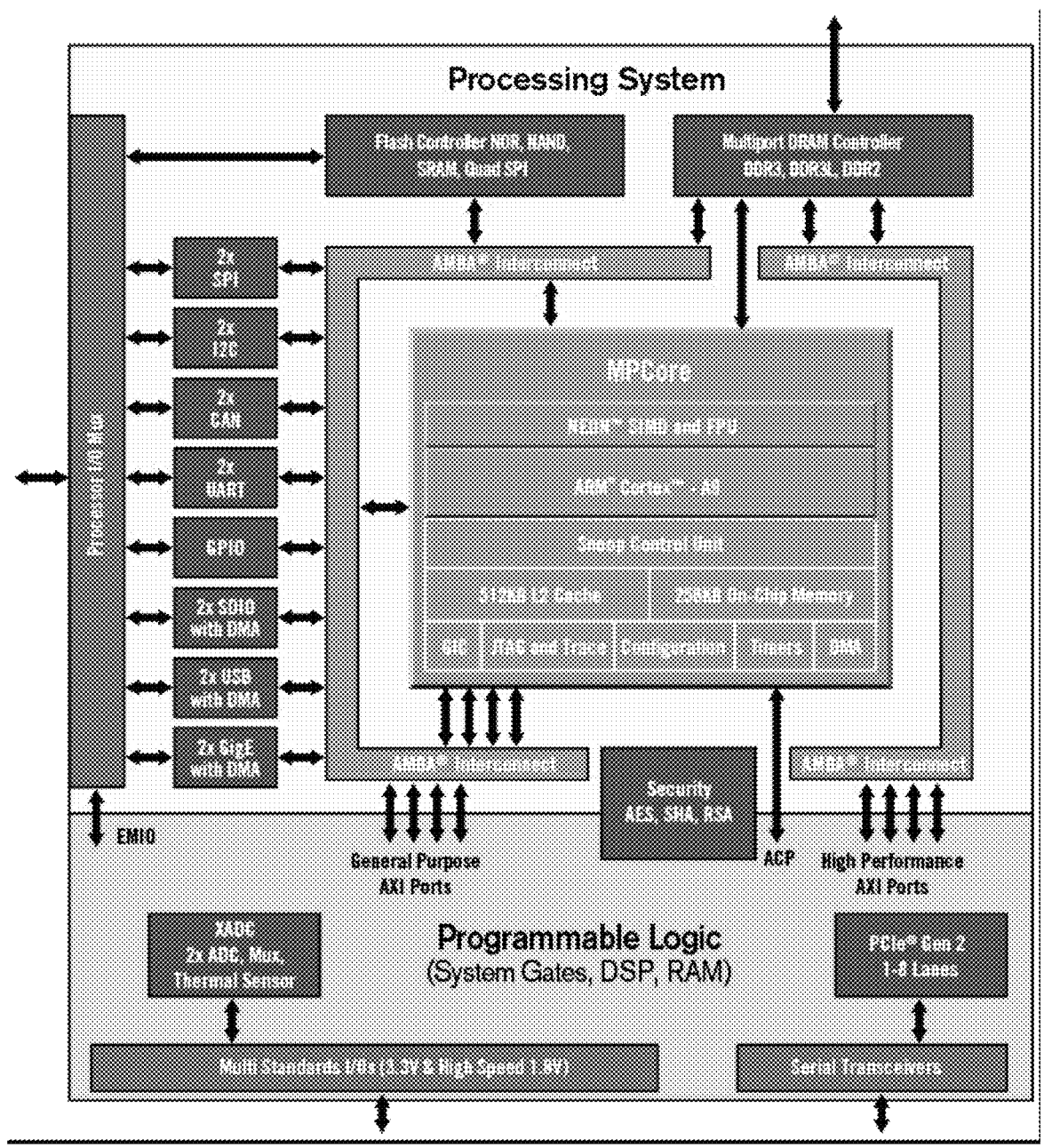

FIGURE 13 - Xilinx Zynq-7000s SoC
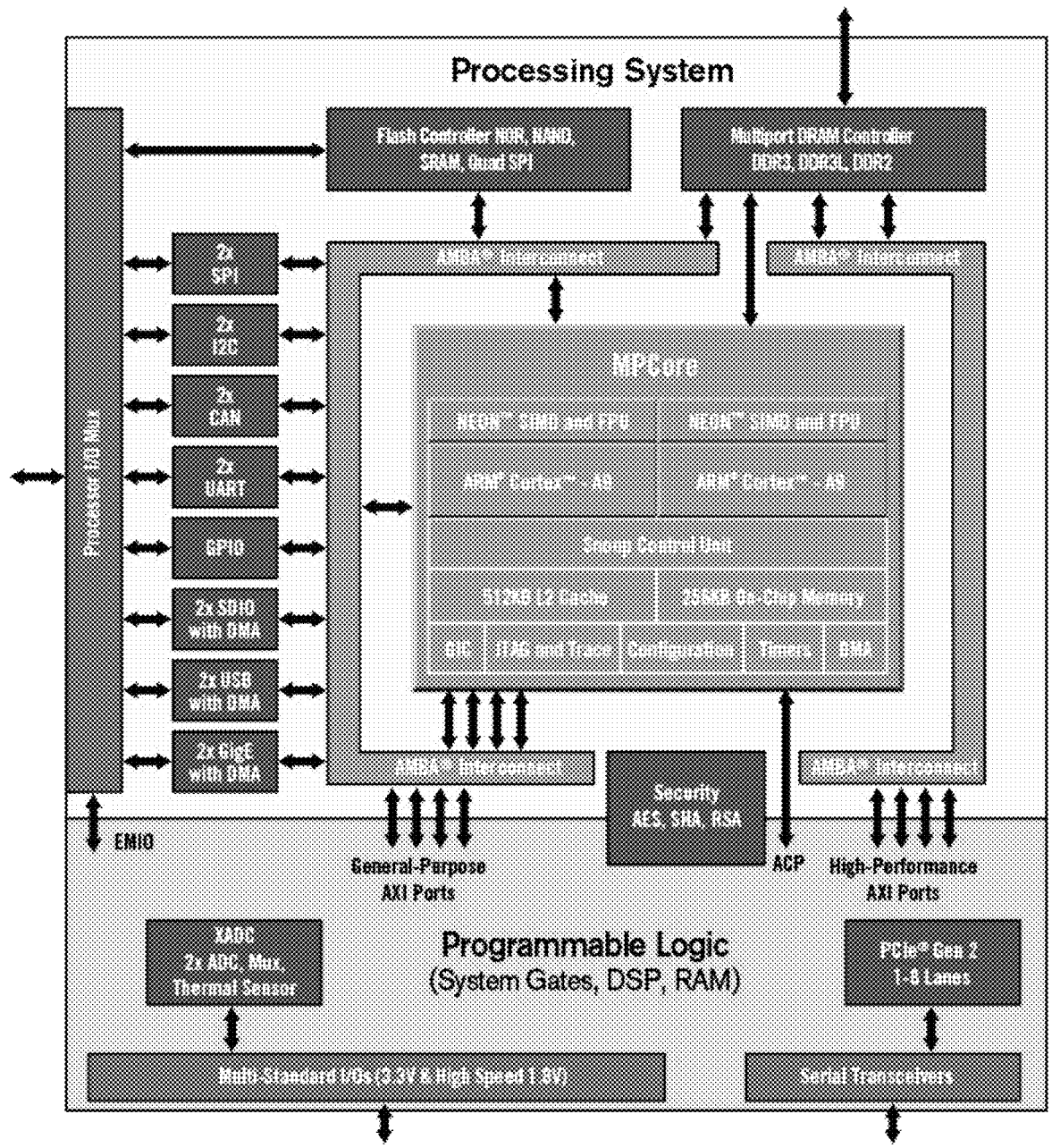

APPARATUS AND METHOD OF REAL-TIME HEALTH AND EXERCISE SENSOR MECHANISM WITH BIOPOTENTIAL ELECTRODE INTEGRATED DOUBLE 3D GYROSCOPE NETWORK

CROSS REFERENCE TO RELATED APPLICATIONS

None.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO A SEQUENCE LISTING

Not applicable.

BACKGROUND

Field of the Invention

This present invention is generally directed towards electronic human prosthetics, and specifically to an integrated sensor mechanism using a pair of 3D gyroscopes and a pair of biopotential electrodes to sense real-time 3D motions of spine and ribcage simultaneously with ECG signals.

Background of the Invention

BRIEF SUMMARY OF THE INVENTION

In preferred embodiments, there are provided devices for, and methods of using, an integrated sensor mechanism using a pair of 3D gyroscopes and a pair of biopotential electrodes to sense real-time 3D motions of spine and ribcage simultaneously with ECG signals.

In one non-limiting embodiment, there is provided a bi-directional body-machine interface (BMI) device, comprising:

(i) a biocompatible container housing an ultrasonic wireless power module, said power module comprises a piezoelectric composite transducer connected to a power rectifier circuit, and a rechargeable battery, wherein the piezoelectric composite transducer forms an internal part of a wireless two-part ultrasonic power transmission system having an external piezoelectric composite transducer paired with the internal part for wirelessly transferring power to recharge the rechargeable battery;

(ii) a wireless RF communication System on Chip (SoC) within the housing, said SoC having a processor core, a memory, and powered by the power module, said processor core configured to control wireless data transmission and reception, said processor core configured to control charging of the rechargeable battery, said processor core configured to acquire sensor output data, said processor core configured to acquire first gyroscope input pulses and second gyroscope input pulses, said processor core configured to analyze normalized motion sensor data, said processor core configured to control stimulation input pulses, said memory configured to store sensor data, and said SoC configured to use low-power near field wireless communication;

(iii) a sensor electronics module that interfaces with the SoC and comprises a digital electrophysiology interface chip, a programmable amplifier, an analog to digital converter, a serial peripheral interface (SPI), an electrocardiography biopotential signals (ECG signals) sensor, and a body temperature sensor, wherein the sensor electronics module is configured to record electrocardiography biopotential signals (ECG signals), and wherein the sensor electronics module is configured to record body temperature signals;

(iv) a first Biopotential Electrode Integrated 3D Gyroscope (BEIG-3D) module connected to the SoC, wherein the BEIG-3D module comprises a first gyroscope sensor and a first gyroscope motion processor, wherein the first BEIG-3D module is enclosed in a first titanium case and the first gyroscope sensor is mounted on an external surface of the first titanium case, wherein the first gyroscope sensor is configured to receive three-dimensional motion sensor data, and the first gyroscope processor is configured to generate accurate sensor fusion data in the format of Quaternions from the received three-dimensional motion sensor data, said first gyroscope processor is configured to use Quaternions sensor fusion data for removing motion related artifacts, said first gyroscope processor is configured normalize the Quaternions sensor fusion data and transmit normalized first motion sensor data to SoC through a first communication cable for motion analysis in a motion analysis module of the SoC; and, (v) a second Biopotential Electrode Integrated 3D Gyroscope (BEIG-3D) module connected to the SoC, wherein the second BEIG-3D module comprises a second gyroscope sensor and a second gyroscope motion processor, wherein the second BEIG-3D module is enclosed in a second titanium case and the second gyroscope sensor is mounted on an external surface of the second titanium case, wherein the second gyroscope sensor is configured to receive three-dimensional motion sensor data, and the second gyroscope processor is configured to generate accurate sensor fusion data in the format of Quaternions from the received three-dimensional motion sensor data, said second gyroscope processor is configured to use Quaternions sensor fusion data for removing motion related artifacts, said second gyroscope processor is configured normalize the Quaternions sensor fusion data and transmit normalized second motion sensor data to SoC through a second communication cable for motion analysis in a motion analysis module of the SoC; and (vi) a stimulation module that interfaces with the SoC and comprises a pulse circuit configured to transmit electrical stimuli.

In another preferred embodiment, there is provided a BMI device further comprising at least one cardiac electrode connected to the stimulation module for transmitting electrical stimulation to the heart.

In another preferred embodiment, there is provided a BMI device, wherein the biocompatible container is a circular disc having a diameter ranging from 25-100 mm, and a height ranging from 8-30 mm.

In another preferred embodiment, there is provided a BMI device, wherein the biocompatible container is a circular disc having a diameter ranging from 28-75 mm, and a height ranging from 10-20 mm.

In another preferred embodiment, there is provided a BMI device, wherein the biocompatible container is a circular disc having a diameter ranging from 30-50 mm, and a height ranging from 10-20 mm.

In another preferred embodiment, there is provided a BMI device, wherein the biocompatible container is a circular disc having a diameter less than or equal to 35 mm, and a height less than or equal to 10 mm.

In another preferred embodiment, there is provided a BMI device, wherein the biocompatible container is comprised of one or more a materials selected from the group consisting of a metal, a polymer, or a composite.

In another preferred embodiment, there is provided a BMI device, wherein the biocompatible container is comprised of one or more a materials selected from the group consisting of titanium, Nitinol(R), surgical steel, calcium, copper, zinc, iron, cobalt, magnesium, manganese, vanadium, molybdenum, silicate, strontium, tungsten, chromium, nickel, aluminum, and ceramics, composites, alloys, compounds, and mixtures thereof.

In another preferred embodiment, there is provided a BMI device, wherein the biocompatible container is comprised of one or more a materials selected from the group consisting of polyurethane (PU), polyesters, polyethers (PEEK), silicones, silicates, poly(vinyl chloride) (PVC), acrylates, methacrylates, dextran, synthetic rubber (cis-polyisoprene), polyvinyl acetate, Bakelite, polychloroprene (neoprene), nylon, polystyrene, poly-ethylene, polypropylene, polyacrylonitrile, polyvinyl butyral (PVB), poly(vinylidene chloride), fluorinated polymers, polytetrafluoroethylene (PTFE), and mixtures and copolymers thereof.

In another preferred embodiment, there is provided a BMI device, wherein the biocompatible container comprises a biocompatible coating selected from calcium phosphate, tricalcium phosphate, or hydroxyapatite.

In another preferred embodiment, there is provided a BMI device, wherein the rechargeable battery is a Lithium ion battery.

In another preferred embodiment, there is provided a BMI device, wherein the processor core is configured to turn off module components that are not active to conserve battery.

In another preferred embodiment, there is provided a BMI device, wherein the low power near-field wireless communication comprises a 2.4 GHz protocol.

In another preferred embodiment, there is provided a BMI device, wherein the low power near-field wireless communication has a data rate ranging from 250 Kbps-2 Mbps.

In another preferred embodiment, there is provided a BMI device, wherein the low power near-field wireless communication comprises a Bluetooth Low Energy (BLE) communication protocol or an Enhanced ShockBurst (ESB) protocol.

In another preferred embodiment, there is provided a BMI device, wherein the low power near-field wireless communication has a transmit power ranging from 0.01-2.5 mW (−20 dBm to 4 dBm).

In another preferred embodiment, there is provided a BMI device, wherein the low power near-field wireless communication has a minimum data rate bandwidth of 1.5 Mbits/sec.

In another preferred embodiment, there is provided a BMI device, wherein the analog to digital converter is 16-bit.

In another preferred embodiment, there is provided a BMI device, wherein the sensor electronics module includes a built-in temperature sensor, and wherein the SoC is configured to monitor tissue temperature and implement device changes to avoid tissue damage from high temperatures.

In another preferred embodiment, there is provided a BMI device, wherein the sensor electronics module is configured to record at least 32 channels of motion related activity.

In another preferred embodiment, there is provided a BMI device, wherein the pulse circuit is configured to generate at least 16 channels of stimulation.

In another preferred embodiment, there is provided a BMI device, wherein the pulse circuit is configured to generate at least 32 channels of stimulation.

In another preferred embodiment, there is provided a BMI device, wherein the pulse circuit is configured to generate bi-phase pulses.

In another preferred embodiment, there is provided a BMI device, wherein the sensor electronics module is configured to record at least 32 channels of motion related activity and wherein the pulse circuit is configured to generate at least 32 channels of stimulation.

In another preferred embodiment, there is provided a BMI device, wherein the SoC is configured to monitor at least 32 channels of recorded motion related activity and wherein SoC is configured to direct the pulse circuit to generate stimulation to a pre-programmed channel of stimulation based on recorded motion related activity.

In another preferred embodiment, there is provided a BMI device, wherein the SoC is configured to implement multiplexing of signals for stimulation and signals for recording.

In another preferred embodiment, there is provided a BMI device, wherein the SoC is configured to perform simultaneous power charging and wireless data transmission.

In another preferred embodiment, there is provided a BMI device, further comprising a memory device connected to the SoC.

In another preferred embodiment, there is provided a BMI device, further comprising a remote computer in wireless communication with the SoC.

In another preferred embodiment, there is provided an integrated body-machine interface system, comprising at least two of the BMI devices described herein, wherein the BMI devices are configured to communicate and operate in a closed-loop, wherein a first BMI device is configured to transmit a signal to a second BMI device that is configured to receive the signal, and wherein the first BMI device is configured to generate the signal when the SoC of the first BMI device records motion related activity, and wherein the second BMI device is configured to direct electrical stimuli when the SoC of the second BMI receives the signal.

In another preferred embodiment, there is provided an integrated BMI system, comprising three of the BMI devices described herein, wherein the BMI devices are configured to communicate and operate in a closed-loop, wherein the BMI devices are configured to transmit and receive signals to and from each other, wherein a first BMI device is configured to generate the signal when the SoC of the first BMI device records motion related activity, and wherein the second BMI device is configured to direct cardiac electrical stimuli when the SoC of the second BMI receives the signal, and wherein the third BMI device is configured to generate a second signal when the SoC of the third BMI device records temperature, and wherein the first BBMI device is configured to direct electrical stimuli when the SoC of the first BMI receives the second signal.

In another preferred embodiment, there is provided a method of transmitting a signal from a BMI device to a computer, comprising the steps: Deploying or implanting the device described herein onto the torso of a patient with the sensors in operative communication with the body of the patient; and, transmitting a signal from the device to an external receiver.

In another preferred embodiment, there is provided a method of treating a patient in need thereof, comprising the steps of: Deploying or implanting the device described herein onto the torso of a patient in need thereof; transmitting and receiving signals to and from the device to treat a disease or disorder, or track conditions selected from the group consisting of: sleep apnea, asthma, vital sign monitoring, exercise monitoring, drowsy driving, and biometric authentication.

In another preferred embodiment, there is provided a method of treating a patient in need thereof, comprising the steps of: Deploying or implanting the device of claim 1 onto the torso of a patient in need thereof; transmitting and receiving signals to and from the device to treat a disease or disorder, or track conditions, wherein the device stimulates a cardiac nerve, a glossopharyngeal nerve, or a diaphragm nerve.

BRIEF DESCRIPTION OF THE DRAWINGS

FIG. 12 is a integrated circuit chip block diagram for a Zynq-7000S device and shows a single-core ARM Cortex™-A9 processor mated with 28 nm Artix®-7 based programmable logic, 6.25 Gb/s transceivers and outfitted with commonly used hardened peripherals.

FIG. 13 is a integrated circuit chip block diagram for a Xilinx Zynq-7000 device and shows dual-core ARM Cortex-A9 processors integrated with 28 nm Artix-7 or Kintex®-7 based programmable logic, up to 6.6M logic cells, and with transceivers ranging from 6.25 Gb/s to 12.5 Gb/s.

DETAILED DESCRIPTION OF THE INVENTION

Figure 1:
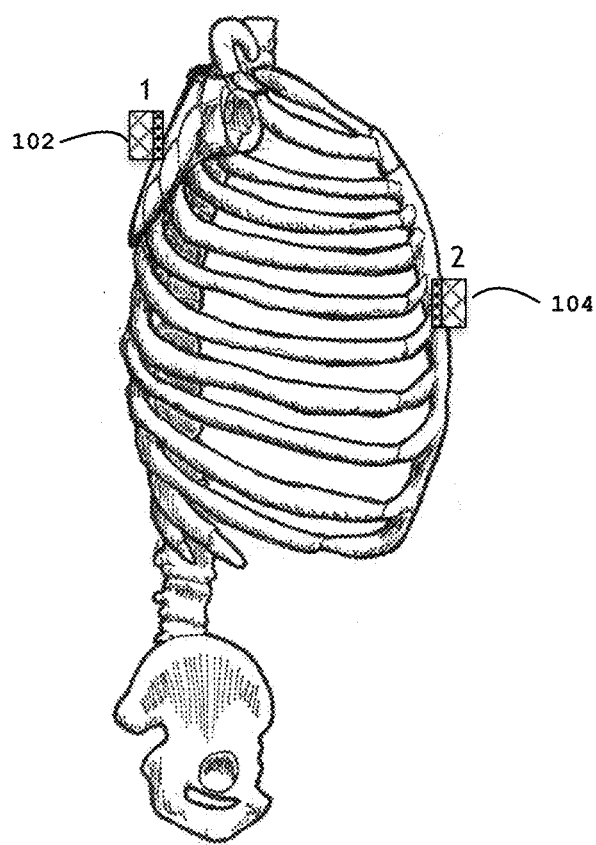
FIG. 1 is an illustration of a human torso skeleton including ribcage, sternum, spine, and pelvis, and show an implantable (or wearable) biomedical sensing system with two-3D gyroscopes (or IMUs) and integrated biopotential electrodes. (1: gyroscope A and negative (or positive) polarity biopotential electrode, 2: gyroscope B and positive (or negative) polarity biopotential electrode).

The features, aspects and advantages of the present invention will become better understood with reference to the following description, examples, and claims.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Definitions

To facilitate understanding of the invention, certain terms as used herein are defined below as follows:

As used herein, the term "biocompatible" defines a two-way response, i.e. the body's response to the material and the materials response to the body's environment. The biocompatibility of a medical device refers to the ability of the device to perform its intended function, with the desired degree of incorporation in the host, without eliciting any undesirable local or systemic effects in that host. In preferred embodiments the biocompatible material of the invention is a medical grade or an implant grade material.

The term "closed loop" refers to a way in which we can accurately control a process by monitoring its output and "feeding" some of it back to compare the actual output with the desired output so as to reduce the error and if disturbed, bring the output of the system back to the original or desired response. The measure of the output is called the "feedback signal" and the type of control system which uses feedback signals to control itself is called a Close-loop System. A Closed-loop Control System, also known as a feedback control system is a control system which uses the concept of an open loop system as its forward path but has one or more feedback loops (hence its name) or paths between its output and its input. The reference to "feedback", simply means that some portion of the output is returned "back" to the input to form part of the systems excitation. Closed-loop systems are designed to automatically achieve and maintain the desired output condition by comparing it with the actual condition. It does this by generating an error signal which is the difference between the output and the reference input. In other words, a "closed-loop system" is a fully automatic control system in which its control action being dependent on the output in some way.

As used interchangeably herein, the terms "ECG" and "electrocardiography" refer to the technique of recording the electrical activity of the heart by means of electrodes placed directly on the skin. In a conventional 12-lead ECG, 10 electrodes are placed on the surface of the chest and on the patient's limbs. The overall magnitude of the heart's electrical potential is then measured from 12 different angles ("leads") and is recorded over a period of time (usually 10 seconds). In this way, the overall magnitude and direction of the heart's electrical depolarization is captured at each moment throughout the cardiac cycle. The graph of voltage versus time produced by this noninvasive medical procedure is referred to as an electrocardiogram As used interchangeably herein, the term "body-computer interface", refer to a signal-processing circuit that takes input in the form of raw signals and converts the raw signals to a processed signal that can be input to a digital device for storage and further analysis.

As used herein, the term "system" refers to an organized scheme of multiple components including at least one device as defined above, that together with secondary device(s), serve the function of translating raw signals to an output of a device, where the raw signals are derived from the body of a user of the system. The system may also optionally include a remote computer (non-implanted) that is used to record signals, send stimuli instructions, upgrade the software/firmware of the components, and so forth.

As used herein, the term "device" refers to a piece of equipment or a mechanism designed to serve a special purpose or function. In the examples, the device is a cursor on a video monitor. Other examples of devices within the intended meaning of the term include, without limitation, wheelchairs and prosthetics. The term also embraces mechanisms that can be used to control other mechanisms, such as steering wheels, joysticks, levers, buttons and the like.

As used herein, "low power" means less than 6 milliAmperes for transmitting and receiving, from a supply voltage of 2.0-3.5 V.

As used herein, "high data rate" means 200 kbps up to 1 Gbps, with data rates dependent on the particular modulation schemes used, the BER chosen, the SNR, and power consumption.

As used herein, "treatment" means reducing, eliminating, or ameliorating one or more signs or symptoms, temporarily or more permanently, during the treatment process or upon completion of the treatment process, of a disease, condition, or pathology generally recognized as a medical condition, diagnosis, complaint, or issue.

Conditions and/or uses contemplated as within the scope of the present invention include without limitation: sleep apnea, asthma, vital sign monitoring, exercise monitoring, drowsy driving, and biometric authentication.

Specific nerves that may be stimulated using the device herein include one or more cardiac nerves to treat cardiac abnormalities, one or more glossopharyngeal or related nerves to treat sleep apnea, and one or more nerves associated with the diaphragm to treat asthma and other respiratory disorders or conditions.

As used herein, the term "electrodes" refers to electrical components that deliver electrical charge to target tissue. Electrodes also include the leads that connect them to the pulse generators. Leads and electrodes must be durable as implants. Electrodes include epineural and cuff/encircling electrodes, as well as epimysial and intramuscular electrodes. Electrodes are preferably made from corrosion resistant materials such as platinum, iridium, stainless steel, or alloys. Electrodes may also include a Dacron backing to encourage ingrowth and permanence. Leads are commonly made from stainless steels, and alloys of Co, Cr, and Ni.

FIGURES

Referring now to the Figures, FIG. 1 shows an illustration of the skeleton of a human torso and shows a non-limiting preferred embodiment of an implantable (or wearable) biomedical sensing system with two-3D gyroscopes (or IMUs) and integrated biopotential electrodes. Gyroscope A 102 and negative (or positive) polarity biopotential electrode. Gyroscope B 104 and positive (or negative) polarity biopotential electrode.

Thus, FIG. 1 shows that the invention is an implantable (or wearable) biomedical sensing system with two-3D gyroscopes (or IMUs) 102, 104 and integrated biopotential electrodes. The two 3D IMUs on human skeletal structure (e.g., spine and ribcage bones) build up a simple robotic link consisting of two rotating joints that rotate with a three DOF each.

Figure 2:
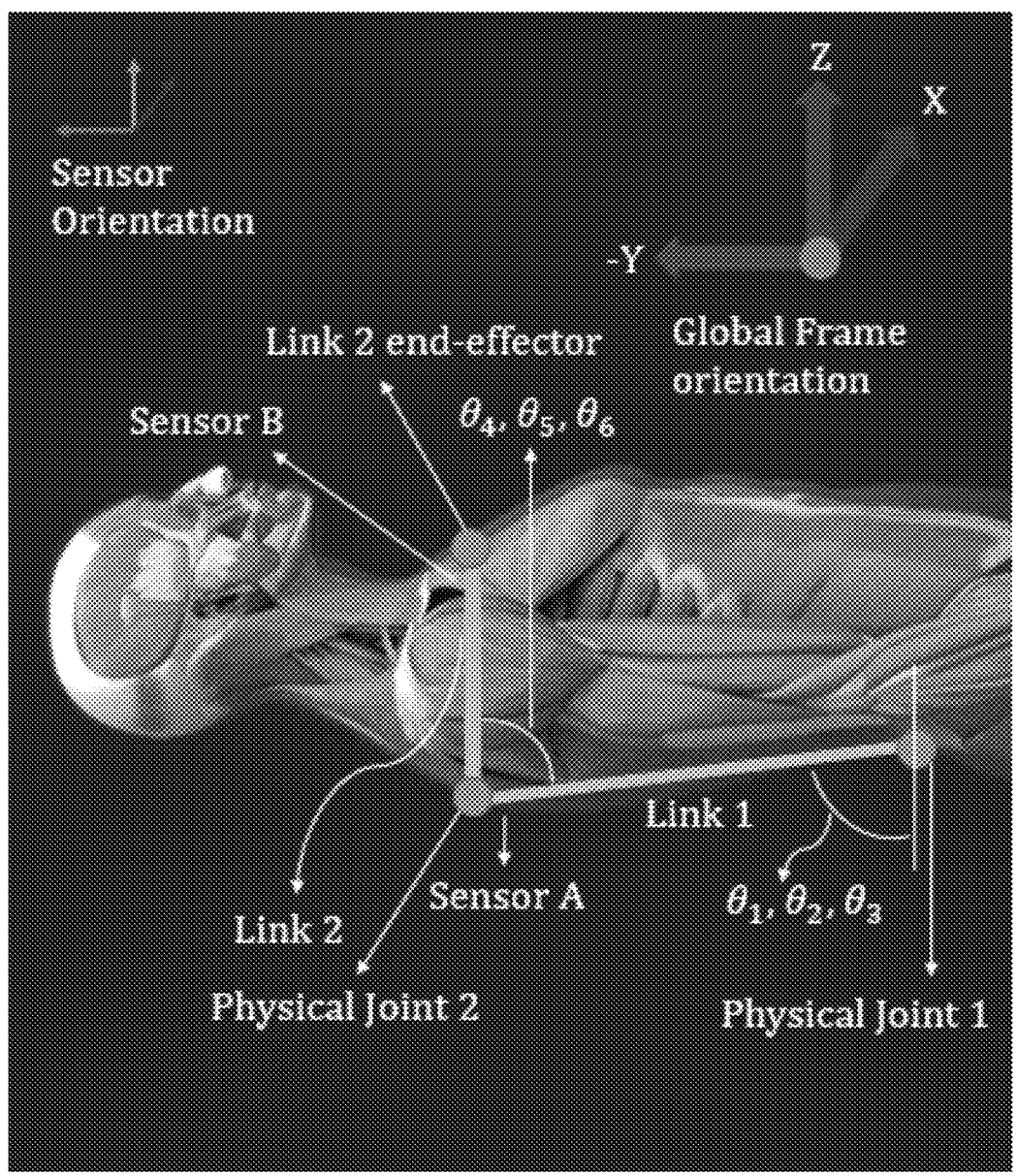
FIG. 2 is an illustration of human torso and head in a supine position, and shows the inverse kinematic calculation of the six joint angles.

FIG. 2 is an illustration of human torso and head in a supine position, and shows the inverse kinematic calculation of the six joint angles.

The inverse kinematic calculation of the six joint angles defined in FIG. 2 provides the accurate decomposition of the two joints. The IMU-link provides a novel body kinematics monitoring system for various medical and sports application.

Computational Algorithm of Trunk and Respiratory Motion

A crucial part of this application of the device is selection of location for placement of the sensors. Three criteria were followed in choosing the location—(1) Sensor A should majorly detect trunk motion (2) Sensor B should experience both trunk and respiratory motion.

Thus, the inverse kinematic calculation of the six joint angles is shown in FIG. 2.

This invention contributes towards the development of mathematical calculations to obtain the relative orientation/motion between the two IMU sensors. These calculations are explained further ahead in this section.

The data obtained from the IMU sensors is in the form of quaternions whose general form is:

Equation $$q = q_0 + q_1 \vec{i} + q_2 \vec{j} + q_3 \vec{k}, \quad (1)$$

Quaternions are an extension of complex numbers. A quaternion has a scalar and a vector part as shown in Equation 1. Term '' in the equation is the scalar quantity, whereas, vector part is a 3-dimensional quantity and is equivalent to the later part of the equation. Note that . . . are real numbers and . . . are imaginary units. Quaternions are converted to Euler angles (more specifically, Tait-Bryan angles) using the following equations—

Equation $$\phi = \arctan \frac{2(q_0 q_1 + q_2 q_3)}{1 - 2(q_1^2 + q_2^2)}, \quad (2)$$

$$\theta = \arcsin(2(q_0 q_2 - q_3 q_1)), \quad (3)$$

-continued $$\psi = \arctan\frac{2(q_0 q_3 + q_1 q_2)}{1 - 2(q_2^2 + q_3^2)},\qquad(4)$$

Here, $\phi$ is roll which portrays rotation around the local/sensor x-axis, $\theta$ is pitch denoting rotation around the y-axis and $\psi$ is yaw representing rotation around the z-axis of sensor. Each quaternion (with 4 quantities) gives a set of Euler angles (having 3 quantities). These Euler angels are substituted into the following matrix in the sequence roll-pitch-yaw to obtain a rotation matrix.

Equation $$R = \begin{bmatrix} c_\theta c_\phi & s_\psi s_\theta c_\phi - c_\psi s_\phi & c_\psi s_\theta c_\phi + s_\psi s_\phi \\ c_\theta s_\phi & s_\psi s_\theta s_\phi + c_\psi c_\phi & c_\psi s_\theta s_\phi - s_\psi c_\phi \\ -s_\theta & s_\psi c_\theta & c_\psi c_\theta \end{bmatrix},\qquad(5)$$

This matrix corresponds to ZYX rotation sequence of Tait-Bryan angles, where 'c' stands for cosine and 's' stands for sine of the respective Euler angle. The Euler angles and rotation matrices are found for both the sensors separately; these give the orientation of each sensor with respect to the global coordinate frame.

Next, the Denavit-Hartenberg (D-H) Convention is applied which assigns right handed frames to links connecting two joints. D-H algorithm is used to derive Forward Kinematics to find the position and orientation of end-effector of robot when all the joint angles are known.

Figure 3:
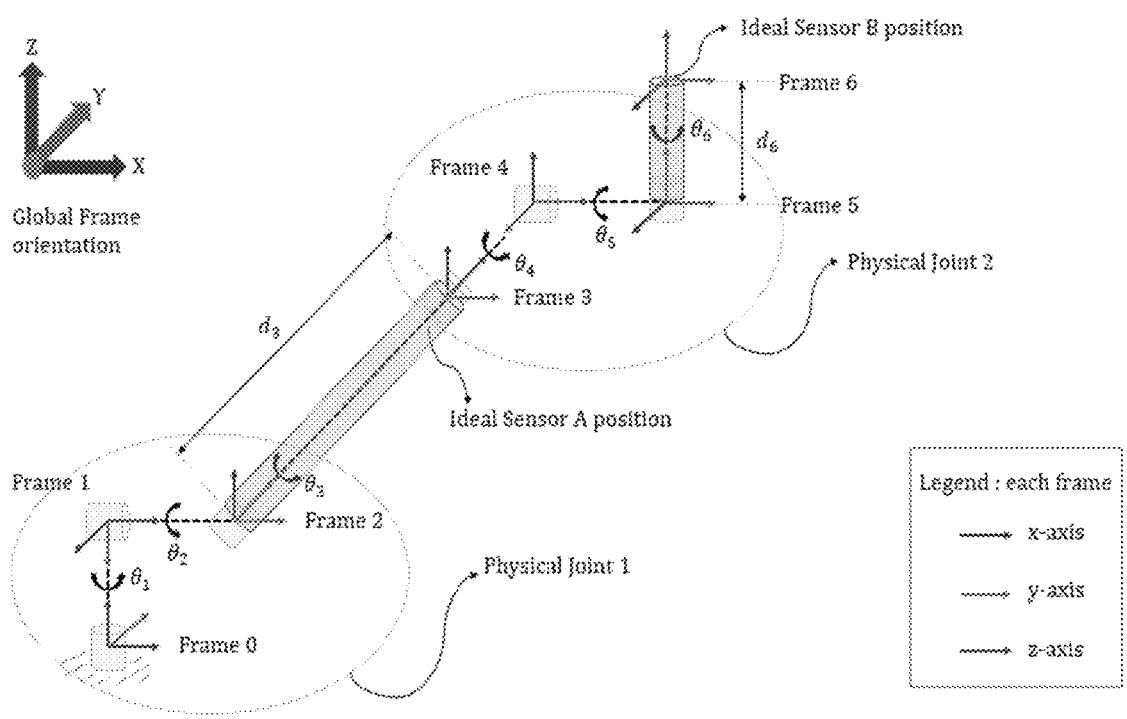
FIG. 3 is an illustration showing x-axis, y-axis, and z-axis in a global frame orientation, and shows the Denavit-Hartenberg (D-H) convention of the double sensor kinematic coordinate system.

FIG. 3 is an illustration showing x-axis, y-axis, and z-axis in a global frame orientation, and shows the Denavit-Hartenberg (D-H) convention of the double sensor kinematic coordinate system.

The four parameters of each link give a homogeneous transformation matrix $A_i$. Thus, 6 homogeneous transformation matrices are obtained. $T_n^0 = A_1 \ldots A_n$ gives the position and orientation information of robot's end-effector (frame n) in base frame (frame 0) i.e. transformation or mapping of frame n in frame 0. $T_n^0$ is of the form of a homogeneous transformation matrix. As in this research, only Rotational part of the 4×4 homogeneous transformation matrix is considered, as per the model geometry and theoretical knowledge, Rotation matrix obtained from Eq. 5 for both the sensors A and B is equivalent to the rotational part of $T_3^0$ and $T_6^0$, or analogously $T_3^G$ and $T_6^G$ since $T_0^G$ is an identity matrix, i.e.—

Equation $$R_{3\times 3}(A) = R_{3\times 3}(T_3^0) = R_{3\times 3}(T_3^G),\qquad(6)$$

$$R_{3\times 3}(B) = R_{3\times 3}(T_{6(original)}^0) = R_{3\times 3}(T_6^G),\qquad(7)$$

The Forward Kinematic Equation to obtain the end-effector (frame 6) orientation in/with respect to base frame (frame 0) is given as follows—

Equation $$T_6^G = T_0^G * T_3^0 * T_6^3\qquad(8)$$

Rearranging the above equation to get orientation of sensor B with respect to sensors A or equivalently the orientation of frame 6 woth respect to frame 3—

Equation $$T_{link21} = T_6^3 = (T_3^0)^{-1} * (T_0^G)^{-1} * T_6^0,\qquad(9)$$

Where, $T_6^0$ is the initialized version of $T_{6(original)}^0$.

First, by applying Inverse Kinematics to $T_3^0$, joint angles $\theta_1$, $\theta_2$, $\theta_3$, that link 1 makes with respect to robot model (frame 0) are obtained.

Equation $$r_{33} = c_2,\quad \theta_2 = \cos^{-1}(r_{33}),\qquad(10)$$

$$r_{31} = -s_2 c_3,\quad \theta_3 = \cos^{-1}\left(\frac{-r_{31}}{s_2}\right),\qquad(11)$$

$$r_{13} = c_1 s_2,\quad \theta_1 = \cos^{-1}\left(\frac{r_{13}}{s_2}\right),\qquad(12)$$

Next, by applying Inverse Kinematics to $T_6^3$, relative joint angles $\theta_4$, $\theta_5$, $\theta_6$ that link 2 makes with link 1 are obtained.

Equation $$r_{33} = c_5,\quad \theta_5 = \cos^{-1}(r_{33}),\qquad(13)$$

$$r_{31} = -s_5 c_6,\quad \theta_6 = \cos^{-1}\left(\frac{-r_{31}}{s_5}\right),\qquad(14)$$

$$r_{13} = c_4 s_5,\quad \theta_4 = \cos^{-1}\left(\frac{r_{13}}{s_5}\right),\qquad(15)$$

System Architecture

The sensor/electrodes can be connected to the sensor circuit using electric cables or using wireless communication technologies such as Bluetooth, ultrasonic, electromagnetic, etc. The onboard computation in the main circuit can provide intelligent data prioritization to handle the different nature of emergencies and notifies the healthcare provider automatically using the commercial network. Further, the device can provide a fully closed-loop system with additional biopotential electrodes for electrical stimulation.

Figure 4:
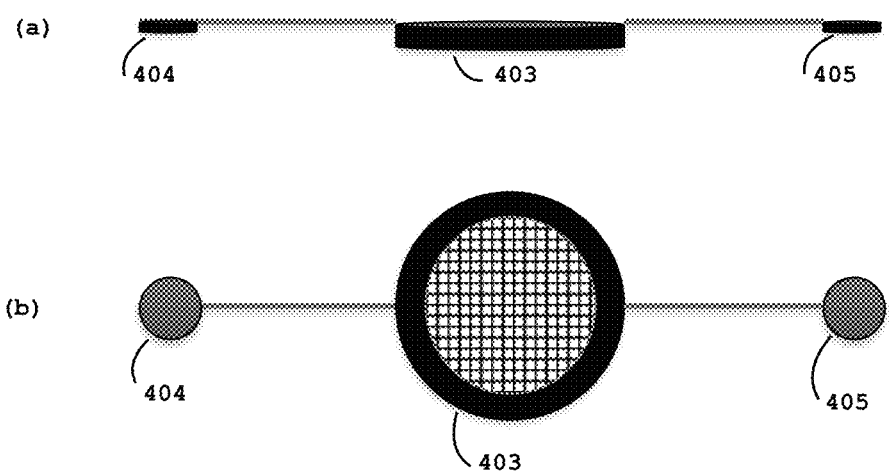
FIG. 4 is an illustration showing a two views of one embodiment of a hardware system, and shows a plane view (top) and a top view (bottom).

FIG. 4 is an illustration showing a two views of one embodiment of a hardware system, and shows (a) a plane view (top) and (b) a top view (bottom). The hardware system includes the following components in the system as shown in FIG. 4.

FIG. 4 shows sensor circuit unit 403 connected to sensors 404, 405, includes a fully integrated electrophysiology amplifier array with on-chip 16-bit analog-to-digital converter (ADC) and industry-standard serial peripheral interface (SPI) for acquiring the biopotential signals (ECG signals). With temperature sensor built on the chip, body temperature can also be monitored. Further, the circuit may include an internal data logging memory for storing data. Further, it can include a wireless communication module to provide a low power communication interface. The transmission of the data in the memory can be conducted to dump the internal memory into a PC or a mobile device. In the case of an "emergency situation," the module will communicate the case with a user and a service provider such as a hospital. Also, a wireless power module to convert ultrasonic energy to electric energy using PMN-PT piezoelectric membrane can be included. The module delivers the power to charge a Li-Ion rechargeable battery. Our prototype system can be powered up by one 3.0-3.7 V Li-Ion rechargeable battery.

Referring now to FIGS. 5-8, experimental results show that it is clear that the developed body kinematics monitoring system can decompose body motions from the two 3D gyroscope signals to accurately detect chest-breathing motion. The developed system can be used for various medical and sports application including sleep apnea research.

Figure 5:
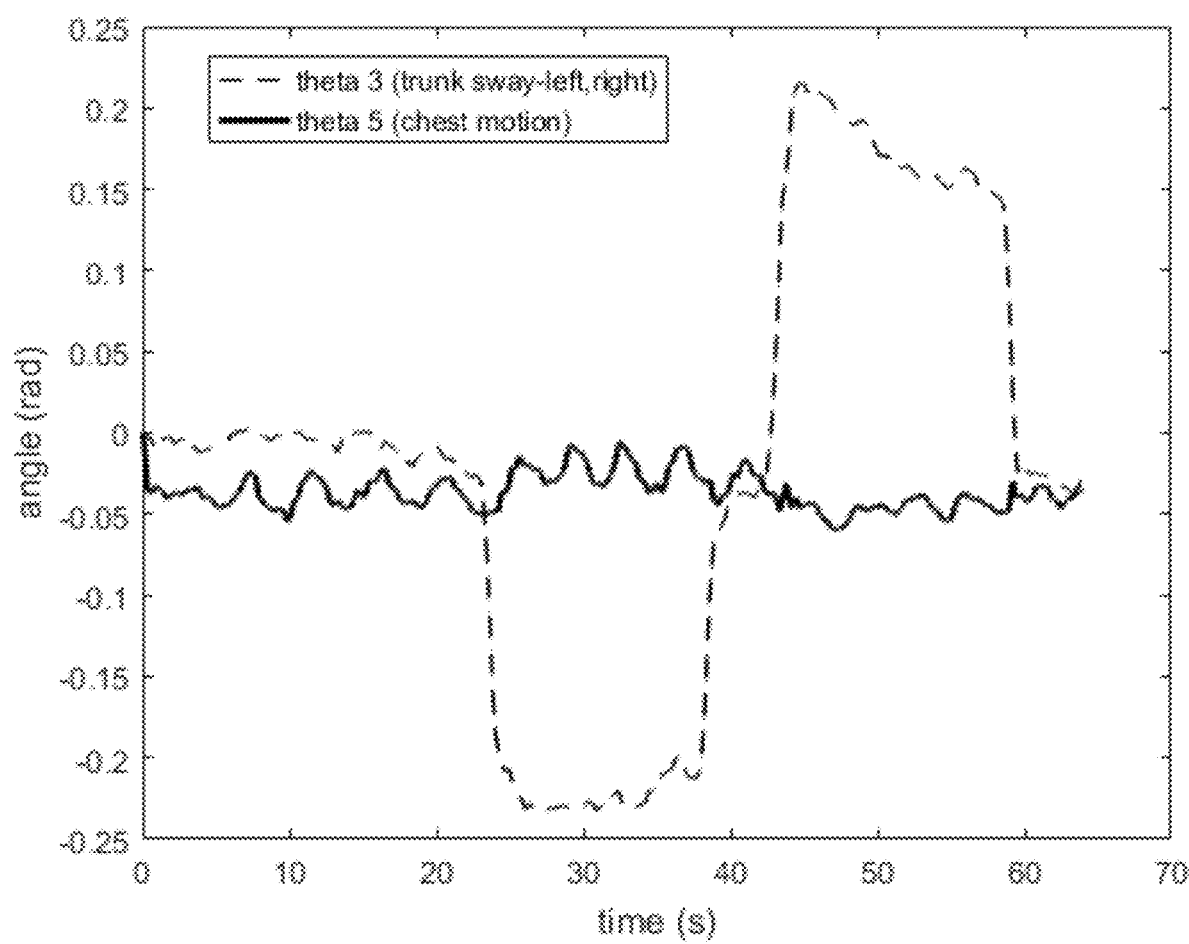
FIG. 5 is a line graph of angle (x-axis) over time (y-axis), and shows experimental data with Left-right swing motion of the spine and the chest upward-downward motion.

FIG. 5 is a line graph of angle (x-axis) in radians over time (y-axis) in seconds, and shows experimental data with Left-right swing motion of the spine (theta 3) and the chest upward-downward motion (theta 5).

Figure 6:
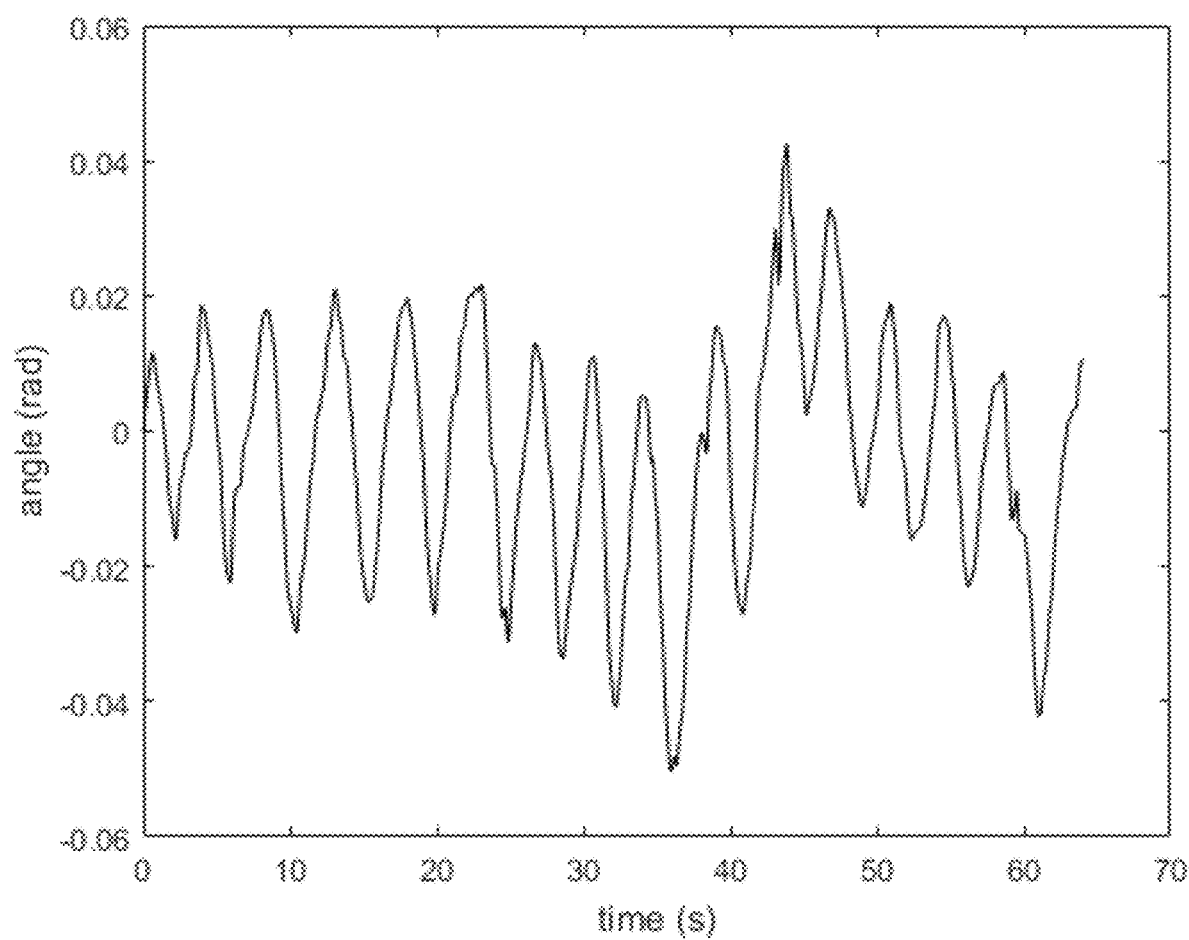
FIG. 6 is a line graph of angle (x-axis) over time (y-axis), and shows experimental data: with real-time breathing signals measured from the breathing motion analysis system.

FIG. 6 is a line graph of angle (x-axis) in radians over time (y-axis) in seconds, and shows experimental data: with real-time breathing signals measured from the breathing motion analysis system. FIG. 6 shows about 2-3 breaths every 10 seconds. FIG. 6 shows the angle ranging from about 0.02 to −0.02 radians for the first 25 seconds. FIG. 6 shows a decrease in angle at seconds 25 to 35 s, an increase in angle at seconds 35 to 45 s, followed by a decrease in angle at seconds 45-65 s.

Figure 7:
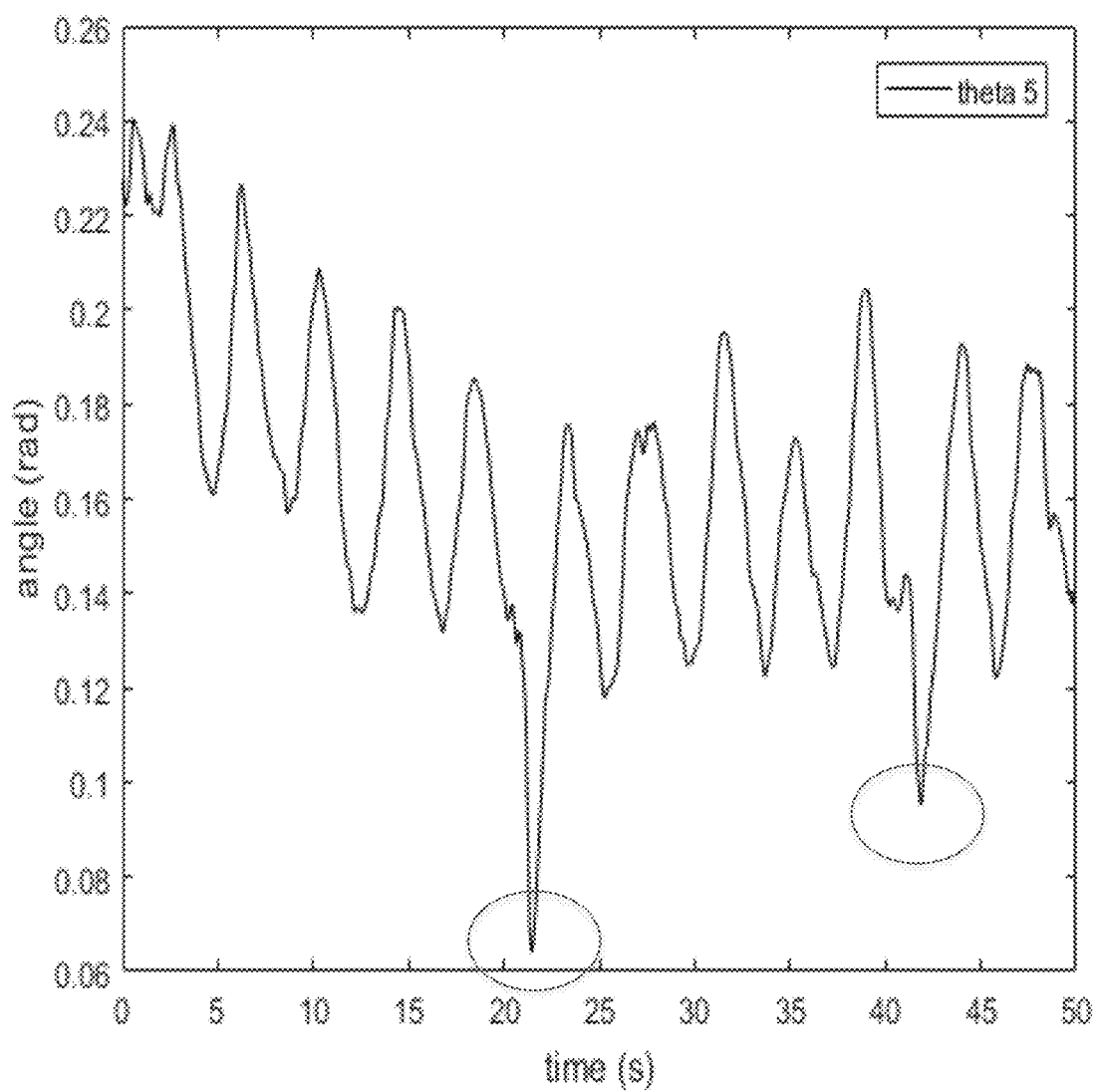
FIG. 7 is a line graph of angle (x-axis) over time (y-axis), and shows experimental data with breathing motion along with a single coughing pattern after every five breaths.

FIG. 7 is a line graph of angle (x-axis) over time (y-axis), and shows experimental data with breathing motion along with a single coughing pattern after every five breaths. The first coughing pattern occurs at time 22 s, and the second occurs at about time 42 s.

Figure 8:
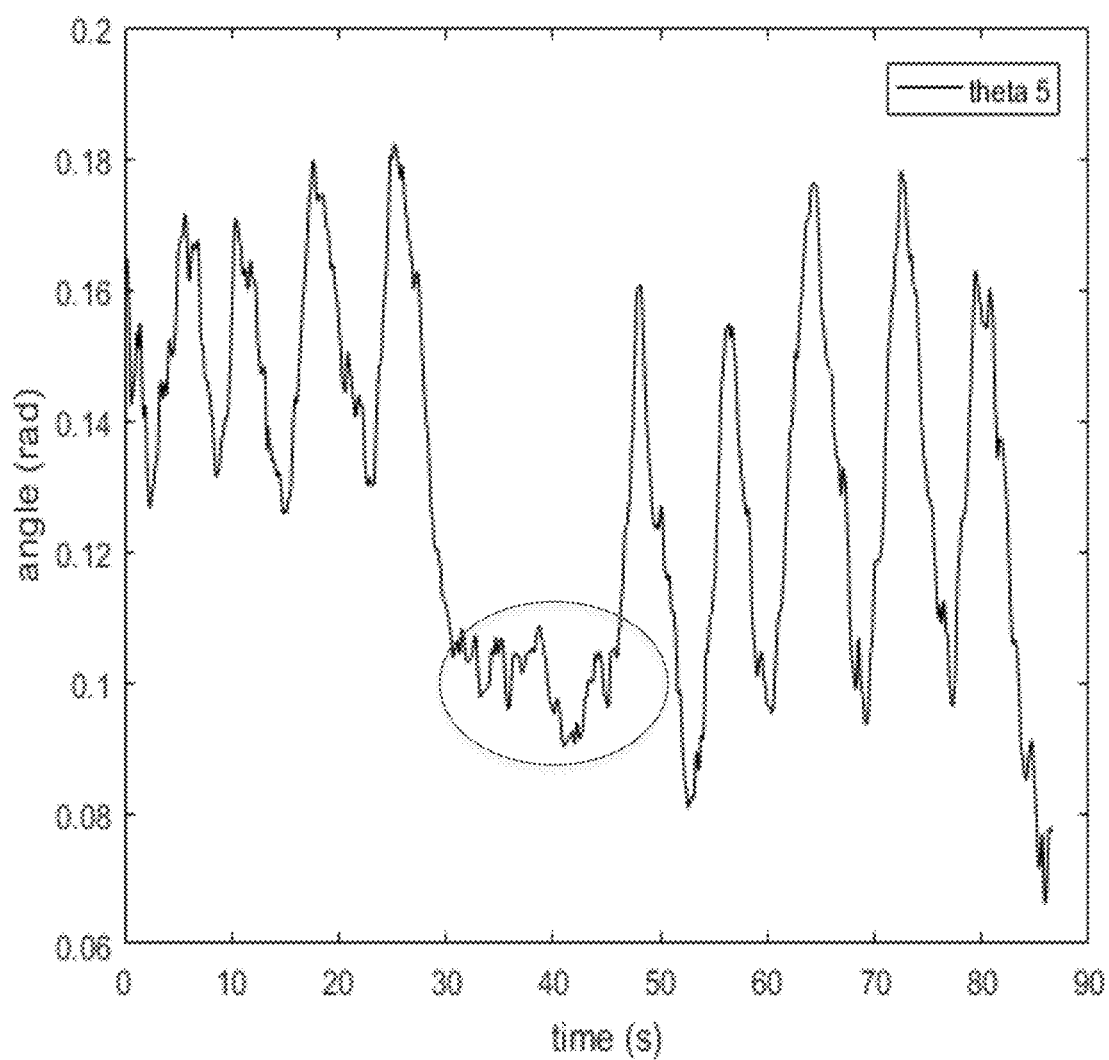
FIG. 8 is a line graph of angle (x-axis) over time (y-axis), and shows experimental data with breathing motion with a 10-s breath-hold episode to mimic sleep apnea.

FIG. 8 is a line graph of angle (x-axis) over time (y-axis), and shows experimental data with breathing motion with a 10-s breath-hold episode to mimic sleep apnea. FIG. 8 shows from time 30-45 s the motion remaining at about 0.1 radians, before resuming the periodic waveform range from about 0.1 to about 0.18 radians.

Figure 9:
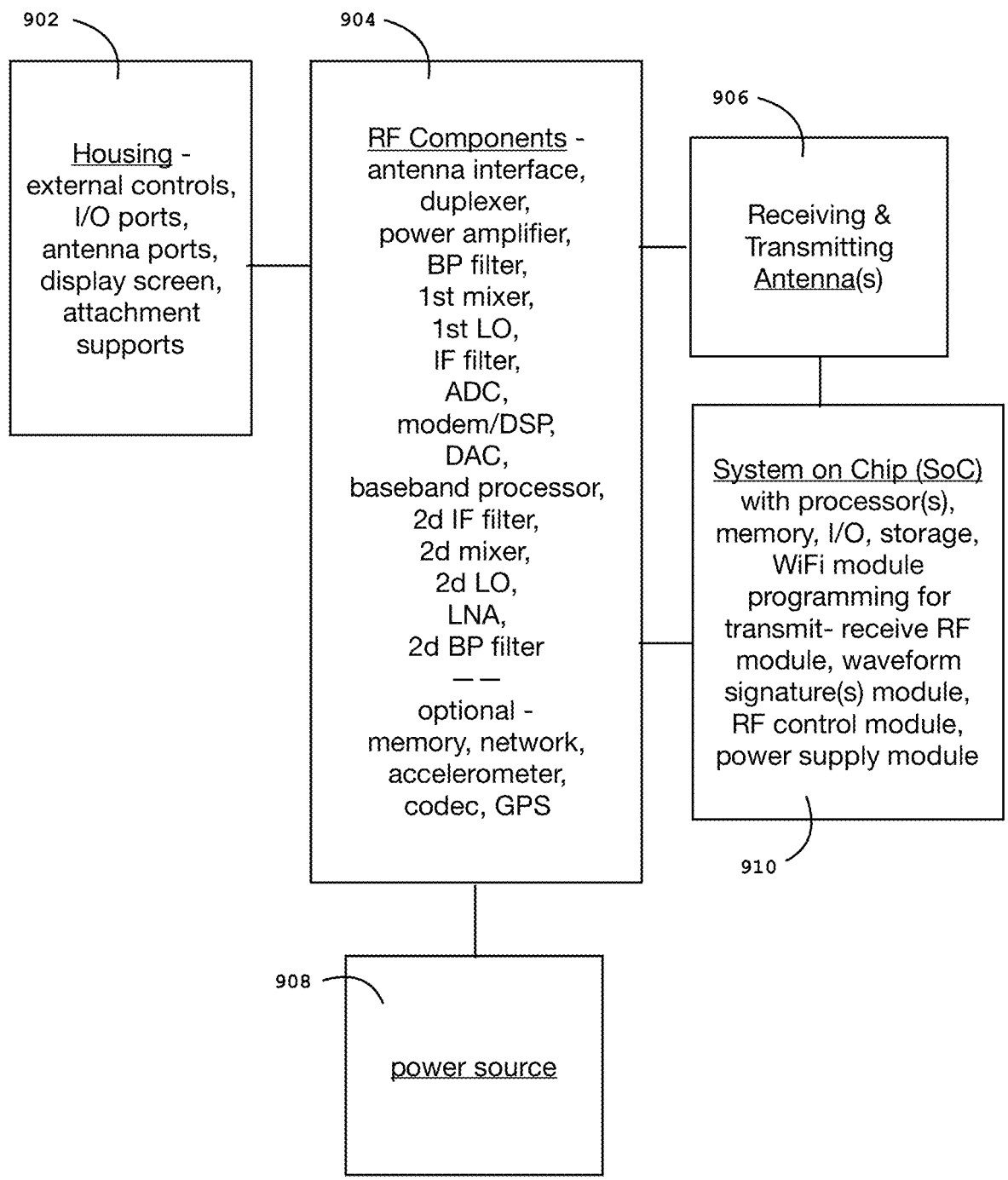
FIG. 9 is a block diagram of standard RF components that can be used for transmitting a t various frequencies.

FIG. 9 is a block diagram and shows standard RF components board for sending and receiving, and processing, RF signals. The "Radio-Frequency or RF components" refers to antenna(s), duplexer, power amplifier, bandpass filter, 1st mixer, 1st Local Oscillator, intermediate frequency filter, modem, baseband processor, 2d IF filter, 2d mixer, 2d LO, Low Noise Amplifier, 2d BP filter, and optionally may include one or more accelerometers, codec, GPS unit, and repeaters. FIG. 9 shows in a non-limiting example, the system may comprise a housing 902, RF components 904, antennas 906, processing such as a System on Chip 910, and a power source 912. The housing 902 includes external controls, I/O ports, antenna ports, a display screen, and stabilizer supports (legs). The RF components 904 include antenna interface, duplexer, power amplifier, BP filter, 1st mixer, 1st LO, IF filter, ADC, modem/DSP, DAC, baseband processor, 2d IF filter, 2d mixer, 2d LO, LNA, and 2d BP filter. The RF components may also optionally include memory, network card-ports-processor, accelerometer, a CODEC, a GPS receiver and processor, repeater, and duplicate, redundant electronic pathways and circuitry to make the unit radiation-hardened. The System on Chip (SoC) 910 includes processor(s), memory, I/O, storage, WiFi module programming for transmit-receive RF module, waveform signature(s) module, RF control module, and a power supply module.

Memory, as used herein, includes without limitation PROM, Flash, SDRAM, EEPROM. It is also contemplated that the RF components may include may include specialized processors such as Field Programmable Gate Arrays (FPGAs) and Application Specific Integrated Chips (ASICs). Referring to the housing, it is contemplated as within the scope of the invention that the housing may be constructed of metal, metal alloy, polymer, ceramic, and composite materials. The housing may be a unitary construction, or, may be assembled in a modular manner. The housing may be water-proofed using gaskets, seals, and coatings.

Example—Biopotential electrode integrated 3D gyroscope (or IMU) #1

Figure 10:
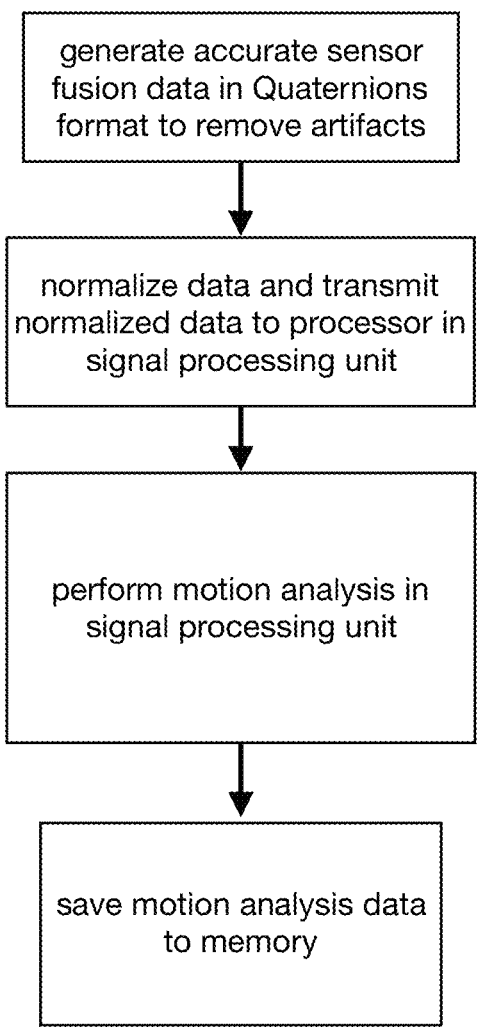
FIG. 10 is a flowchart of one preferred embodiment of a process using the device described herein.

Referring now to FIG. 10, the gyroscope motion processor generates accurate sensor fusion data in the format of Quaternions, which can be essential in removing motion related artifacts. The Quaternions are then normalized and send it to an onboard computing processor in the signal-processing unit through communication cable for motion analysis. Also, a biopotential electrode #1 (negative) is placed on a biocompatible titanium enclosing case.

Example—Biopotential electrode integrated 3D gyroscope (or IMU) #2

Figure 11:
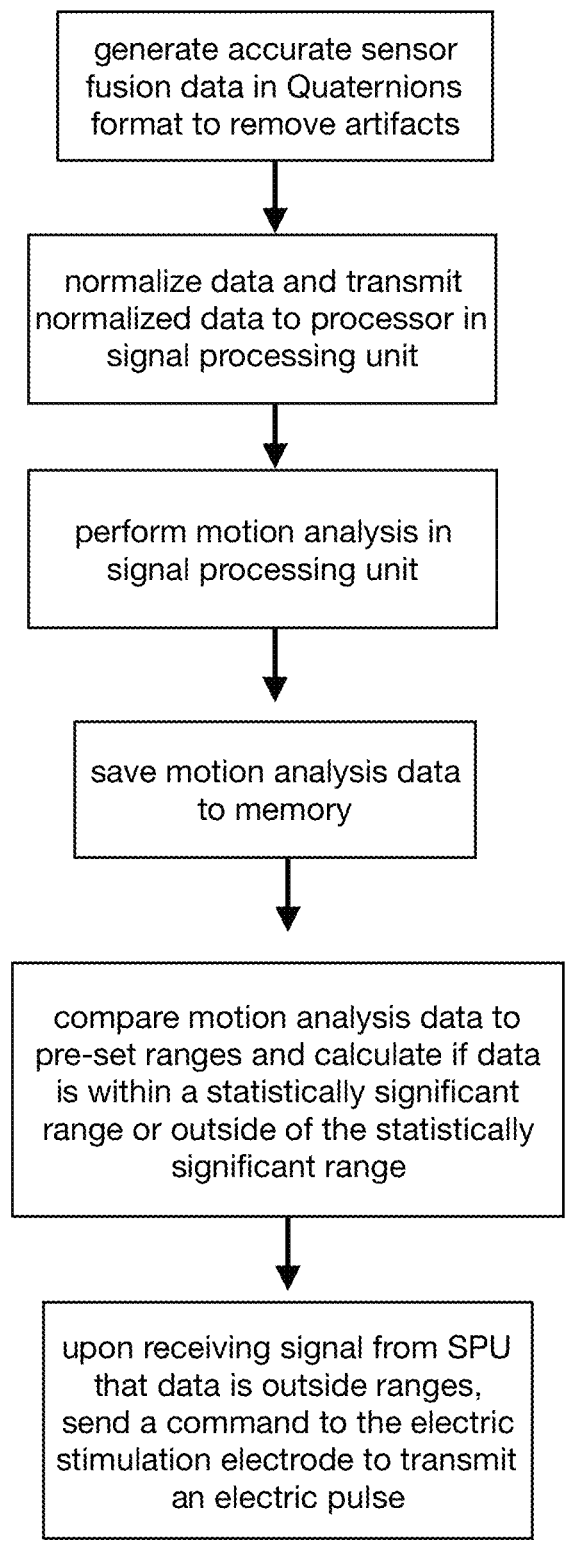
FIG. 11 is another flowchart of another non-limiting preferred embodiment of a process using the device described herein.

Referring now to FIG. 11, the gyroscope motion processor generates accurate sensor fusion data in the format of Quaternions, which can be essential in removing motion related artifacts. The Quaternions are then normalized and send it to an onboard computing processor in the signal-processing unit through communication cable for motion analysis. Also, a biopotential electrode #2 (positive) is placed on a biocompatible titanium enclosing case.

Further, an electric stimulation electrode can be included for a closed-loop intervention treatment.

Uses and conditions to which the device(s) can be applied include using the sensor mechanism to monitor the following health and exercise symptoms, monitoring vital signs, treating or monitoring sleep apnea, treating or monitoring asthma, monitoring vital signs during sport/exercise, athlete tracking, avoiding drowsy driving, and providing biometric authentication.

FIG. 12 shows in a non-limiting example, the device/system includes in a preferred embodiment, a "System on Chip", or SoC. SoC refers to an integrated circuit chip that integrates all or most of the components of a computer or electronic system. SoC usually includes (i) one or more microcontroller, microprocessor or digital signal processor (DSP) core(s), (ii) memory blocks including a selection of ROM, RAM, EEP-ROM and flash memory, (iii) timing sources/clock signal generators, including oscillators and phase-locked loops to control execution of SoC functions, (iv) peripherals including counter-timers, real-time timers and power-on reset generators, (v) external interfaces and programming for communication protocols including WiFi, Bluetooth, cellular, USB, FireWire, Ethernet, USART, SPI, and HDMI, (vi) analog interfaces including analog-to-digital converters and digital-to-analog converters, (vii) voltage regulators and power management circuits, and/or (viii) a computer bus to connect the different components, also called "blocks", of the System-on-Chip, and/or (ix) direct memory access controllers to route data directly between external interfaces and memory, bypassing the CPU or control unit, thereby increasing the data throughput (the amount of data processed per time) of the SoC. Examples of commercially available SoCs include Xilinx SoCs that are processor-centric platforms that offer software, hardware and I/O programmability in a single chip.

Referring now to FIG. 12, the Zynq-7000 family is based on the SoC architecture. Zynq-7000 products incorporate a dual core ARM Cortex-A9 based Processing System (PS) and Xilinx Programmable Logic in a single device. FIG. 12 is a integrated circuit chip block diagram for a Zynq-70005 device and shows a single-core ARM Cortex™-A9 processor mated with 28 nm Artix®-7 based programmable logic, 6.25 Gb/s transceivers and outfitted with commonly used hardened peripherals.

FIG. 13 is a integrated circuit chip block diagram for a Xilinx Zynq-7000 device and shows dual-core ARM Cortex-A9 processors integrated with 28 nm Artix-7 or Kintex®-7 based programmable logic, up to 6.6M logic cells, and with transceivers ranging from 6.25 Gb/s to 12.5 Gb/s.

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

The invention claimed is:

1. A bi-directional body-machine interface (BMI) device, comprising:
   (i) a biocompatible container housing an ultrasonic wireless power module, said power module comprises a piezoelectric composite transducer connected to a power rectifier circuit, and a rechargeable battery, wherein the piezoelectric composite transducer forms an internal part of a wireless two-part ultrasonic power transmission system having an external piezoelectric composite transducer paired with the internal part for wirelessly transferring power to recharge the rechargeable battery;
   (ii) a wireless RF communication System on Chip (SoC) within the housing, said SoC having a processor core, a memory, and powered by the power module, said processor core configured to control wireless data transmission and reception, said processor core configured to control charging of the rechargeable battery, said processor core configured to acquire sensor output data, said processor core configured to acquire first gyroscope input pulses and second gyroscope input pulses, said processor core configured to analyze normalized motion sensor data, said processor core configured to control stimulation input pulses, said memory configured to store sensor data, and said SoC configured to use low-power near field wireless communication;
   (iii) a sensor electronics module that interfaces with the SoC and comprises a digital electrophysiology interface chip, a programmable amplifier, an analog to digital converter, a serial peripheral interface (SPI), an electrocardiography biopotential signals (ECG signals) sensor, and a body temperature sensor, wherein the sensor electronics module is configured to record electrocardiography biopotential signals (ECG signals), and wherein the sensor electronics module is configured to record body temperature signals;
   (iv) a first Biopotential Electrode Integrated 3D Gyroscope (BEIG-3D) module connected to the SoC, wherein the BEIG-3D module comprises a first gyroscope sensor and a first gyroscope motion processor, wherein the first BEIG-3D module is enclosed in a first titanium case and the first gyroscope sensor is mounted on an external surface of the first titanium case, wherein the first gyroscope sensor is configured to receive three-dimensional motion sensor data, and the first gyroscope processor is configured to generate accurate sensor fusion data in the format of Quaternions from the received three-dimensional motion sensor data, said first gyroscope processor is configured to use Quaternions sensor fusion data for removing motion related artifacts, said first gyroscope processor is configured normalize the Quaternions sensor fusion data and transmit normalized first motion sensor data to SoC through a first communication cable for motion analysis in a motion analysis module of the SoC; and,
   (v) a second Biopotential Electrode Integrated 3D Gyroscope (BEIG-3D) module connected to the SoC, wherein the second BEIG-3D module comprises a second gyroscope sensor and a second gyroscope motion processor, wherein the second BEIG-3D module is enclosed in a second titanium case and the second gyroscope sensor is mounted on an external surface of the second titanium case, wherein the second gyroscope sensor is configured to receive three-dimensional motion sensor data, and the second gyroscope processor is configured to generate accurate sensor fusion data in the format of Quaternions from the received three-dimensional motion sensor data, said second gyroscope processor is configured to use Quaternions sensor fusion data for removing motion related artifacts, said second gyroscope processor is configured normalize the Quaternions sensor fusion data and transmit normalized second motion sensor data to SoC through a second communication cable for motion analysis in a motion analysis module of the SoC; and
   (vi) a stimulation module that interfaces with the SoC and comprises a pulse circuit configured to transmit electrical stimuli.

2. The BMI device of claim 1, further comprising at least one cardiac electrode connected to the stimulation module for transmitting electrical stimulation to the heart.

3. The BMI device of claim 1, wherein the biocompatible container is a circular disc having a diameter ranging from 25-100 mm, and a height ranging from 8-30 mm.

4. The BMI device of claim 1, wherein the biocompatible container is a circular disc having a diameter ranging from 28-75 mm, and a height ranging from 10-20 mm.

5. The BMI device of claim 1, wherein the biocompatible container is a circular disc having a diameter ranging from 30-50 mm, and a height ranging from 10-20 mm.

6. The BMI device of claim 1, wherein the biocompatible container is a circular disc having a diameter less than or equal to 35 mm, and a height less than or equal to 10 mm.

7. The BMI device of claim 1, wherein the biocompatible container is comprised of one or more a materials selected from the group consisting of a metal, a polymer, or a composite.

8. The BMI device of claim 1, wherein the biocompatible container is comprised of one or more a materials selected from the group consisting of titanium, Nitinol(R), surgical steel, calcium, copper, zinc, iron, cobalt, magnesium, manganese, vanadium, molybdenum, silicate, strontium, tungsten, chromium, nickel, aluminum, and ceramics, composites, alloys, compounds, and mixtures thereof.

9. The BMI device of claim 1, wherein the biocompatible container is comprised of one or more a materials selected from the group consisting of polyurethane (PU), polyesters, polyethers (PEEK), silicones, silicates, poly(vinyl chloride) (PVC), acrylates, methacylates, dextran, synthetic rubber (cis-polyisoprene), polyvinyl acetate, Bakelite, polychloroprene (neoprene), nylon, polystyrene, polyethylene, polypropylene, polyacrylonitrile, polyvinyl butyral (PVB), poly (vinylidene chloride), fluorinated polymers, polytetrafluoroethylene (PTFE), and mixtures and copolymers thereof.

10. The BMI device of claim 1, wherein the biocompatible container comprises a biocompatible coating selected from calcium phosphate, tricalcium phosphate, or hydroxyapatite.

11. The BMI device of claim 1, wherein the rechargeable battery is a Lithium ion battery.

12. The BMI device of claim 1, wherein the processor core is configured to turn off module components that are not active to conserve battery.

13. The BMI device of claim 1, wherein the low power near-field wireless communication comprises a 2.4 GHz protocol.

14. The BMI device of claim 1, wherein the low power near-field wireless communication has a data rate ranging from 250 Kbps-2 Mbps.

15. The BMI device of claim 1, wherein the low power near-field wireless communication comprises a Bluetooth Low Energy (BLE) communication protocol or an Enhanced ShockBurst (ESB) protocol.

16. The BMI device of claim 1, wherein the low power near-field wireless communication has a transmit power ranging from 0.01-2.5 mW (−20 dBm to 4 dBm).

17. The BMI device of claim 1, wherein the low power near-field wireless communication has a minimum data rate bandwidth of 1.5 Mbits/sec.

18. The BMI device of claim 1, wherein the analog to digital converter is 16-bit.

19. The BMI device of claim 1, wherein the sensor electronics module includes a built-in temperature sensor, and wherein the SoC is configured to monitor tissue temperature and implement device changes to avoid tissue damage from high temperatures.

20. The BMI device of claim 1, wherein the sensor electronics module is configured to record at least 32 channels of motion related activity.

21. The BMI device of claim 1, wherein the pulse circuit is configured to generate at least 16 channels of stimulation.

22. The BMI device of claim 1, wherein the pulse circuit is configured to generate at least 32 channels of stimulation.

23. The BMI device of claim 1, wherein the pulse circuit is configured to generate bi-phase pulses.

24. The BMI device of claim 1, wherein the sensor electronics module is configured to record at least 32 channels of motion related activity and wherein the pulse circuit is configured to generate at least 32 channels of stimulation.

25. The BMI device of claim 1, wherein the SoC is configured to monitor at least 32 channels of recorded motion related activity and wherein SoC is configured to direct the pulse circuit to generate stimulation to a pre-programmed channel of stimulation based on recorded motion related activity.

26. The BMI device of claim 1, wherein the SoC is configured to implement multiplexing of signals for stimulation and signals for recording.

27. The BMI device of claim 1, wherein the SoC is configured to perform simultaneous power charging and wireless data transmission.

28. The BMI device of claim 1, further comprising a memory device connected to the SoC.

29. The BMI device of claim 1, further comprising a remote computer in wireless communication with the SoC.

30. An integrated body-machine interface system, comprising at least two of the BMI devices of claim 1, wherein the BMI devices are configured to communicate and operate in a closed-loop, wherein a first BMI device is configured to transmit a signal to a second BMI device that is configured to receive the signal, and wherein the first BMI device is configured to generate the signal when the SoC of the first BMI device records motion related activity, and wherein the second BMI device is configured to direct electrical stimuli when the SoC of the second BMI receives the signal.

31. The integrated body-machine interface system of claim 30, comprising three of the BMI devices of claim 1, wherein the BMI devices are configured to communicate and operate in a closed-loop, wherein the BMI devices are configured to transmit and receive signals to and from each other, wherein a first BMI device is configured to generate the signal when the SoC of the first BMI device records motion related activity, and wherein the second BMI device is configured to direct cardiac electrical stimuli when the SoC of the second BMI receives the signal, and wherein the third BMI device is configured to generate a second signal when the SoC of the third BMI device records temperature, and wherein the first BBMI device is configured to direct electrical stimuli when the SoC of the first BMI receives the second signal.

32. A method of transmitting a signal from a BMI device to a computer, comprising the steps:
Deploying or implanting the device of claim 1 onto the torso of a patient with the sensors in operative communication with the body of the patient; and,
transmitting a signal from the device to an external receiver.

33. A method of treating a patient in need thereof, comprising the steps of:
Deploying or implanting the device of claim 1 onto the torso of a patient in need thereof;
transmitting and receiving signals to and from the device to treat a disease or disorder, or track conditions selected from the group consisting of: sleep apnea, asthma, vital sign monitoring, exercise monitoring, drowsy driving, and biometric authentication.

34. A method of treating a patient in need thereof, comprising the steps of:
Deploying or implanting the device of claim 1 onto the torso of a patient in need thereof;
transmitting and receiving signals to and from the device to treat a disease or disorder, or track conditions, wherein the device stimulates a cardiac nerve, a glossopharyngeal nerve, or a diaphragm nerve.

* * * * *